(12) United States Patent
Groenendaal et al.

(10) Patent No.: US 11,903,724 B2
(45) Date of Patent: Feb. 20, 2024

(54) METHOD AND A SYSTEM FOR DETECTING A RESPIRATORY EVENT OF A SUBJECT AND A METHOD FOR FORMING A MODEL FOR DETECTING A RESPIRATORY EVENT

(71) Applicant: Onera Technologies B.V., Eindhoven (NL)

(72) Inventors: Willemijn Groenendaal, Leuven (BE); Dirk Deschrijver, Leuven (BE); Tom Van Steenkiste, Leuven (BE); Joeri Ruyssinck, Leuven (BE)

(73) Assignee: Onera Technologies B.V., Eindhoven (NL)

( * ) Notice: Subject to any disclaimer, the term of this patent is extended or adjusted under 35 U.S.C. 154(b) by 701 days.

(21) Appl. No.: 16/981,931

(22) PCT Filed: Mar. 13, 2019

(86) PCT No.: PCT/EP2019/056222
§ 371 (c)(1),
(2) Date: Sep. 17, 2020

(87) PCT Pub. No.: WO2019/179836
PCT Pub. Date: Sep. 26, 2019

(65) Prior Publication Data
US 2021/0030353 A1 Feb. 4, 2021

(30) Foreign Application Priority Data
Mar. 19, 2018 (EP) ..................... 18162591

(51) Int. Cl.
*A61B 5/00* (2006.01)
*G16H 40/67* (2018.01)
(Continued)

(52) U.S. Cl.
CPC .......... *A61B 5/4818* (2013.01); *A61B 5/0809* (2013.01); *A61B 5/7267* (2013.01);
(Continued)

(58) Field of Classification Search
CPC ... A61B 5/4818; A61B 5/0809; A61B 5/7267; A61B 5/7275; A61B 5/318; A61B 5/0205; G06N 20/20
See application file for complete search history.

(56) References Cited

U.S. PATENT DOCUMENTS

2002/0193697 A1* 12/2002 Cho ..................... A61B 5/0205
607/42
2005/0256420 A1 11/2005 Norman et al.
(Continued)

FOREIGN PATENT DOCUMENTS

WO 2017183039 A1 10/2017

OTHER PUBLICATIONS

International Search Report for International Application No. PCT/EP2019/056222, dated Jun. 13, 2019 (18 pages).
(Continued)

*Primary Examiner* — Chu Chuan Liu
(74) *Attorney, Agent, or Firm* — Kagan Binder, PLLC (57) ABSTRACT

A method for detecting a respiratory event of a subject comprises: receiving a bio-impedance measurement signal (S2) dependent on respiratory action from the subject; extracting (306) at least one time-sequence of the bio-impedance measurement signal (S2); and for each extracted time-sequence: comparing (308) the bio-impedance measurement signal (S2) with each of a plurality of machine learning models in an ensemble of machine learning models to form a set of predictions of occurrence of a respiratory event, wherein each prediction is based on comparing the bio-impedance measurement signal (S2) with one machine
(Continued)

learning model, wherein each model correlates features of time-sequences of a bio-impedance measurement signal (S2) with presence of a respiratory event and wherein each model is trained on a unique data set of training time-sequences; deciding (310) whether a respiratory event occurs in the extracted time-sequence based on the set of predictions.

15 Claims, 5 Drawing Sheets

(51) Int. Cl.
    *G16H 50/70*     (2018.01)
    *G16H 50/20*     (2018.01)
    *G16H 10/20*     (2018.01)
    *G06N 20/20*     (2019.01)
    *A61B 5/08*     (2006.01)
    *G16H 10/60*     (2018.01)

(52) U.S. Cl.
    CPC ........... *A61B 5/7275* (2013.01); *G06N 20/20* (2019.01); *G16H 10/20* (2018.01); *G16H 40/67* (2018.01); *G16H 50/20* (2018.01); *G16H 50/70* (2018.01); *G16H 10/60* (2018.01)

(56) References Cited

U.S. PATENT DOCUMENTS

2013/0172759 A1    7/2013   Melker et al.
2015/0154353 A1    6/2015   Xiang et al.
2017/0367625 A1   12/2017   Auerbach

OTHER PUBLICATIONS

Krawczyk et al., "Ensemble learning for data stream analysis: A survey," Information Fusion, vol. 37, pp. 132-156, 2017, (27 pages).

Gomes et al., "A Survey on Ensemble Learning for Data Stream Classification," ACM Computing Surveys, vol. 50, No. 2, Article 23, Mar. 2017, (37 pages).

Japanese Office Action, and English Translation therefore, for Japanese Application No. 2021-500335, dated Jun. 6, 2023, (15 pages).

* cited by examiner

METHOD AND A SYSTEM FOR DETECTING A RESPIRATORY EVENT OF A SUBJECT AND A METHOD FOR FORMING A MODEL FOR DETECTING A RESPIRATORY EVENT

CROSS-REFERENCE TO RELATED APPLICATIONS

This application claims priority to International Application No. PCT/EP2019/056222, filed Mar. 13, 2019 and titled "BLOCKING MECHANISM FOR A HANDLE ARRANGEMENT," which in turn claims priority from a European Patent Application having Ser. No. 18/162,591.4, filed Mar. 19, 2018 titled "BLOCKING MECHANISM FOR A HANDLE ARRANGEMENT," both of which are incorporated herein by reference in their entireties

TECHNICAL FIELD

The present inventive concept relates to a method and a system for detecting a respiratory event of a subject. The present inventive concept also relates to a training method for forming a model for detecting a respiratory event. In particular, the present inventive concept relates to detection of respiratory events based on a bio-impedance measurement signal.

BACKGROUND

Sleep apnea is one of the most common sleep-related disorders. Many cases of sleep apnea are undiagnosed as patients are rarely aware of their condition. The consequences of sleep apnea are, however, all too severe ranging from increased blood pressure, strokes and heart arrhythmia to critical heart failure.

The gold standard for diagnosing sleep apnea is an overnight polysomnography (PSG) in a dedicated sleep laboratory. Yet, PSG tests are expensive and availability of tests are limited. A large-scale screening of patients using a home testing device would allow the most critical patients to receive earlier diagnoses while patients with no suspected apnea can continue search for correct diagnosis.

Bio-impedance signals are of increasing interest to use for monitoring of health of a subject. A bio-impedance signal may be modulated e.g. by breathing of a subject, and the bio-impedance signal may therefore be used for respiratory monitoring of the subject. This could be used for instance in sleep monitoring applications.

Bio-impedance measurements may be performed with relatively simple equipment causing minimal or at least low inconvenience to the subject on which the bio-impedance measurements are performed. Therefore, use of bio-impedance measurements represent an interesting option in any type of monitoring, analysis or assessment of respiration, e.g. in screening of sleep apnea.

WO 2004/112606 discloses an apparatus that includes means for acquisition of one or more bio-impedance signals, preferably across the thorax providing trans-thoracic measurements and across the neck region providing trans-cervical measurements; means for calculating components of the bio-impedance signals which can be ascribed to cardiac activity or to respiratory effort, means for obtaining measurements from the respiratory effort bio-impedance signal to produce diagnostic measures relating to obstructive and central apneas; and means for obtaining measurements from the cardiac bio-impedance signal which can provide a diagnostic measure of the impact of sleep disordered breathing on cardiac hemodynamic parameters.

Although it is indicated that apnea events may be detected, the apparatus makes use of two separate bio-impedance measurements, which should be detected across the thorax and across the neck region of a patient. Thus, it would still be desirable to have a reliable method of detecting respiratory events without setting very specific requirements on how the bio-impedance measurement signal is to be acquired.

SUMMARY

An objective of the present inventive concept is to improve respiratory monitoring using a bio-impedance signal. A particular objective of the present inventive concept is to provide a reliable detection of respiratory events.

This and other objectives of the present inventive concept are at least partly met by the invention as defined in the independent claims. Preferred embodiments are set out in the dependent claims.

According to a first aspect, there is provided a method for detecting a respiratory event of a subject, said method comprising: receiving a bio-impedance measurement signal from the subject, said bio-impedance measurement signal being dependent on respiratory action of the subject; extracting at least one time-sequence of the bio-impedance measurement signal; and for each of the extracted time-sequences: comparing the bio-impedance measurement signal with each of a plurality of machine learning models in an ensemble of machine learning models so as to form a set of predictions of occurrence of a respiratory event, wherein each prediction in the set is based on comparing the bio-impedance measurement signal with one machine learning model, wherein each model correlates features of time-sequences of a bio-impedance measurement signal with presence of a respiratory event in the time-sequences of the bio-impedance measurement signal and wherein each model is trained on a unique data set of training time-sequences; and deciding whether a respiratory event occurs in the extracted time-sequence based on the set of predictions.

The bio-impedance measurement signal need not be processed for extracting human engineered features, which would supposedly indicate respiratory events. Such human engineered features may potentially miss important markers of respiratory events. On the contrary, according to the present inventive concept, a bio-impedance measurement signal is compared to machine learning models for determining whether a respiratory event occurs. The machine learning model may in training of the model identify features in the bio-impedance measurement signal that are correlated to respiratory events, such that use of the machine learning models may allow making full use of information in the bio-impedance measurement signal for detecting respiratory events.

Thanks to the use of a plurality of machine learning models in an ensemble of machine learning models, respiratory events may be detected in a very robust manner. The plurality of machine learning models allows determination of a set of predictions, such that the plurality of machine learning models contribute to detection of respiratory events and the detection of respiratory events may be based on an aggregated score from a plurality of models. Thus, the detection of respiratory events is less sensitive to a result based on a single machine learning model.

Thanks to the models being trained on unique data sets, the models may identify different correlations between features in the bio-impedance measurement signal and respiratory events. This further contributes to the detection of respiratory events being robust and that respiratory events may be reliably detected.

The present inventive concept allows use of a bio-impedance measurement signal for robust detection of respiratory events. Bio-impedance measurements may be performed using a relatively simple equipment, which may cause no or insignificant inconvenience to the subject being tested. This implies that acquisition of signals for detecting respiratory events will not affect sleep of the subject such that high quality measurements may be performed while the subject is sleeping. Furthermore, the use of plurality of machine learning models enables robust detection of respiratory events even though a relatively simple bio-impedance measurement is made.

The bio-impedance measurement signal being dependent on respiratory action of the subject may for instance be acquired to measure a bio-impedance on or across a thorax of the subject. When a bio-impedance measurement is performed based on electrodes arranged on a thorax of a subject, chest expansion may cause a change in a current path between the electrodes, such that the bio-impedance is changed in relation to a respiratory effort. Also, air has a different impedance than tissue. As an amount of air present in the lungs varies during a respiratory cycle, the bio-impedance is also changed in relation to respiratory airflow.

However, it should be realized that a bio-impedance measurement signal which is dependent on respiratory action of the subject may be acquired in other manners, such as arranging electrodes to measure a bio-impedance in any relation to lungs or airways of the subject, such as in relation to a neck portion of the subject.

A respiratory event may be any event relating to a (temporally) anomalous respiration of the subject. This may include apnea and hypopnea, such as obstructive sleep apnea (OSA), central apnea (CA), obstructive hypopnea, and central hypopnea, and combinations thereof. The detection of a respiratory event may classify the type of respiratory event or may alternatively merely indicate that any respiratory event occurs, without classifying the respiratory event.

The term "unique data set" as used herein should be construed as two models not being trained on identical data sets of training time-sequences. The two data sets used in training of the two models may share one or more training time-sequences, such that a particular training time-sequence may be present in both data sets. However, each data set will also include a training time-sequence which is not present in the other data set. It should also be realized that more than two models may be trained on "unique data sets", such that each model is trained on a data set which is not identical to any data set on which another model is trained.

According to an embodiment, the bio-impedance measurement signal is compared with each of a plurality of machine learning models in an ensemble of machine learning models formed by neural networks with Long-Short Term Memory (LSTM) cells analyzing the unique data sets of training time-sequences.

The use of LSTM cells allows the machine learning models to model temporal aspects in the training time-sequences which enables the machine learning models to extract relevant temporal features and interactions in order to detect respiratory events. In particular, LSTM cells provide a powerful tool for extracting and using temporal information.

According to an embodiment, the bio-impedance measurement signal is compared with each of a plurality of machine learning models in an ensemble of machine learning models formed by training each model on a unique data set that has been formed by balanced bootstrapping of acquired training time-sequences to combine positive time-sequences including a respiratory event, re-used between different data sets, with negative time-sequences not including a respiratory event, wherein at least a plurality of the negative time-sequences are dis-joint between different data sets.

It is an insight of the invention that time-sequences corresponding to no respiratory event are far more common than time-sequences corresponding to respiratory events. However, such imbalance between positive training time-sequences (in which a respiratory event occurs) and negative training time-sequences (in which no respiratory event occurs) may highly affect a quality of the machine learning model based on the training time-sequences.

A straightforward option to balance a data set, called downsampling, is to subsample negative training time-sequences leading to an equal amount of positive and negative training time-sequences. However, this also leads to a large amount of lost information. Another option is to oversample the positive training time-sequences, known as upsampling, leading to an equal amount of positive and negative training time-sequences. However, as a consequence, there will be an overrepresentation of the same positive training time-sequences. This will quickly lead to overfitting on these specific positive training time-sequences, which may severely limit generalization to unseen data of the model trained on the oversampled data set.

By using a balanced bootstrapping of acquired training time-sequences, the training time-sequences may be divided into unique data sets such that each data set is well-balanced between positive and negative training time-sequences. The positive time-sequences may be re-used between different data sets, such that each data set comprises several positive time-sequences, whereas the negative time-sequences may be arranged in separate data sets. In this way, each data set may have a good balance between positive and negative training time-sequences, while information is not discarded in creation of the models.

The negative time-sequences, i.e. all negative time-sequences, may be dis-joint between different data sets. This would imply that a particular negative time-sequence is only used once in the data sets. This may be a preferred manner of achieving the balanced bootstrapping.

However, it is realized that re-using some negative time-sequences between different data sets may have little influence on an overall result of the machine learning models being formed. Therefore, it would be possible to re-use some (e.g. a few) negative time-sequences between different data sets. In such case, a plurality of negative time-sequences may be dis-joint between different data sets, while one or more negative time-sequences may be re-used in two or more data sets.

Since each of a plurality of machine learning models in an ensemble of machine learning models is formed by training each model on a unique data set defined by balanced bootstrapping, the machine learning models may be formed while taking into account all training data in a balanced manner. This facilitates that the machine learning models are well-trained and that the detection of respiratory events may be performed in a robust manner.

According to an embodiment, the data set of training time-sequences have been acquired from the subject for whom respiratory events are detected.

By training models on the same subject for whom respiratory event detection is later to be performed allows the method to be individualized. This implies that the machine learning models may be very well equipped to detect respiratory events for the subject under test.

An individualized model may be advantageously used in long-term monitoring of a subject, e.g. for follow-up of a subject over long time periods.

However, it should be realized that the machine learning models may be trained on general training time-sequences, which do not include or do not merely include training time-sequences of the subject for whom respiratory event detection is later to be performed. For instance, the machine learning models may be trained on large amounts of training time-sequences acquired from a large number of different patients. This may enable the machine learning models to be robust and enable generally detecting respiratory events for any subject. Hence, the machine learning model may be directly used in detection of respiratory events for a subject who has never been involved in training of the machine learning model. Thus, the machine learning model may be quickly used for detection of respiratory events of new patients, e.g. for diagnosing sleep apnea.

According to an embodiment, the method further comprises receiving an additional measurement signal; extracting at least one time-sequence of the additional measurement signal, wherein the at least one time-sequence of the additional measurement signal corresponds to a simultaneous time period with the at least one time-sequence of the bio-impedance measurement signal; and for each of the extracted time-sequences: comparing the bio-impedance measurement signal and the additional measurement signal with each of a plurality of machine learning models in an ensemble of machine learning models so as to form predictions being included in the set of predictions of occurrence of a respiratory event.

This implies that the method may complement detection of respiratory events using bio-impedance measurement signals with at least one additional measurement. The additional measurement signal may be a measurement of a characteristic of the subject. The measurement signal may directly or indirectly relate to a vital sign and may provide additional information which may be used in detection of respiratory events.

The additional measurement signal may be separately compared with a plurality of machine learning models in the ensemble of machine learning models, such that some machine learning models form predictions based on only the bio-impedance measurement signal and some machine learning models form predictions on only the additional measurement signal. Additionally or alternatively, machine learning models may form predictions based on both the bio-impedance measurement signal and the additional measurement signal.

The use of the additional measurement signal may improve detection of respiratory events, since further information is acquired from the subject. Thus, using additional measurement signal(s), detection of respiratory events may be performed in an even more robust manner. However, it should be realized that an additional measurement signal is not necessary for enabling detection of respiratory events.

The additional measurement signal may be any type of measurement which directly or indirectly provides a measure of e.g. a body temperature of the subject, a heart rate or pulse of the subject, a respiratory rate of the subject or a blood pressure of the subject. The additional measurement signal may for instance be a temperature signal, an electrocardiogram (ECG) signal, or a photoplethysmography (PPG) signal, whereby a direct measurement of a vital sign may be provided. However, the additional measurement signal may alternatively be an accelerometer signal, which may indicate movement of a body part (such as the chest) so as to indirectly provide information of a vital sign as the movement may represent cardiac or pulmonary activity.

The method may comprise receiving a plurality (at least two) additional measurement signals, which may contribute to robust detection of respiratory events.

According to an embodiment, the method further comprises pre-processing the received bio-impedance measurement signal.

The pre-processing of the received bio-impedance measurement signal may ensure that the bio-impedance measurement signal is clean and that the bio-impedance measurement signal represents a respiratory signal. Thus, pre-processing of the received bio-impedance measurement signal may provide an appropriate input for detection of respiratory events. The pre-processing of the received bio-impedance measurement signal may be considered as transforming of the bio-impedance measurement signal into a signal representing respiration of the subject.

The pre-processing of the received bio-impedance measurement signal may include subsampling of an acquired bio-impedance measurement signal.

The pre-processing of the received bio-impedance measurement signal may include extracting a magnitude of a complex-valued signal.

The pre-processing of the received bio-impedance measurement signal may include filtering of the signal, e.g. low-pass filtering of the signal, in order to extract respiratory information. The low-pass filter may be a Butterworth filter or another filter having a zero phase shift.

The pre-processing of the received bio-impedance measurement signal may include removing motion artefacts from the signal.

One or more of the above pre-processing operations may be performed. The pre-processing of the bio-impedance measurement signal may at least partially remove noise and may emphasize information in the bio-impedance measurement signal relating to respiration.

According to an embodiment, the extracting of at least one time-sequence of the bio-impedance measurement signal comprises extracting a plurality of sequential time-sequences of the bio-impedance measurement signal.

Detection of respiratory events may preferably be performed over a relatively long period of time. This may allow analysis of a condition of the subject, e.g. by detecting a frequency of occurrence of respiratory events.

The received bio-impedance measurement signal may thus extend over a long time period and a plurality of sequential time-sequences may be extracted from the received bio-impedance measurement signal.

Each time-sequence of the bio-impedance measurement signal may be separately analyzed in order to determine whether a respiratory event occurs within the time-sequence.

The time-sequences may be partially overlapping. This may improve detection of respiratory events, since at least one time-sequence in a sequence of overlapping time-sequences may include a major portion of a duration of the respiratory event.

In another embodiment, the time-sequences are non-overlapping. This implies that a number of time-sequences may be small (compared to overlapping time-sequences) such that a process of detecting respiratory events may require smaller amount of time and computer resources.

According to an embodiment, the method further comprises determining a measure of respiratory condition of the subject based on comparing a number of time-sequences, for which a decision that a respiratory event occurs has been taken, to a relevant duration period of the bio-impedance measurement signal.

The method may for instance determine a measure according to a standardized methodology, such that the measure of respiratory condition based on the method may be compared to measures obtained in other manners. For instance, the method may include determining an Apnea Hypopnea Index (AHI), which may be determined as a number of respiratory events divided by a total sleep time.

Thus, if the method is to determine an AHI measure, a relevant duration corresponding to sleep time of the subject may be determined. Thus, if the received bio-impedance signal extends over a duration including a time period before the subject falls asleep or including time periods where the subject is awake, such time periods may be removed and not be part of the relevant duration period of the bio-impedance measurement signal.

According to an embodiment, the comparing of the bio-impedance measurement signal with each of a plurality of machine learning models determines a plurality of sets of predictions for occurrences of different respiratory events, and wherein said deciding whether a respiratory event occurs is performed for each set of predictions, wherein the method further comprising outputting a prediction of occurrence of a respiratory event, wherein the outputting differentiates between respiratory events including central sleep apnea, obstructive sleep apnea and hypopnea.

The differentiation between different types of respiratory events enables more detailed analysis of a condition of the subject, as types of respiratory events occurring may be taken into account in the analysis.

Each model may be trained for enabling differentiation between different types of events. The training of the models for detecting different respiratory events may include balanced bootstrapping, by the models being trained on unique data sets which combine positive time-sequences for each type of respiratory event with negative time-sequences, wherein at least a plurality of the negative time-sequences are dis-joint between different data sets and positive time-sequences may be re-used between different data set.

According to a second aspect, there is provided a method for forming a model for detecting a respiratory event of a subject, said method comprising: receiving bio-impedance measurement signals from one or more subjects, said bio-impedance measurement signal being dependent on respiratory action of the subject; extracting a plurality of training time-sequences of the bio-impedance measurement signals; receiving information of occurrences of respiratory events, which information is synchronized with the plurality of training time-sequences so as to classify the training time-sequences as positive time-sequences representing a respiratory event or negative time-sequences not representing a respiratory event; determining a plurality of machine learning models to form an ensemble of machine learning models, wherein each model correlates features of time-sequences of a bio-impedance measurement signal with presence of a respiratory event in the time-sequences of the bio-impedance measurement signal and wherein each model is trained on a unique data set of the plurality of training time-sequences.

Effects and features of this second aspect are largely analogous to those described above in connection with the first aspect. Embodiments mentioned in relation to the first aspect are largely compatible with the second aspect.

The training of the plurality of machine learning models to form an ensemble of machine learning models may allow respiratory events to be detected in a very robust manner based on the trained plurality of machine learning models.

Thanks to the models being trained on unique data sets, the models may identify different correlations between features in the bio-impedance measurement signal and respiratory events. This further contributes to the detection of respiratory events being robust and that respiratory events may be reliably detected.

The information of occurrences of respiratory events may be received based on acquisition of another signal, from which respiratory events may be detected with large certainty. The other signal may be acquired in synchronization with acquisition of the received bio-impedance measurement signal, such that identification of respiratory events in the other signal may be related to a time-sequence of the bio-impedance measurement signal. For instance, the received information of occurrences of respiratory events may be provided from a PSG system.

In another embodiment, the information of occurrences of respiratory events may be received from manual annotation, wherein time-sequence of bio-impedance measurement signals including a respiratory event may be tagged based on manual input.

According to an embodiment, the determining of the plurality of machine learning models comprises using neural networks with Long-Short Term Memory (LSTM) cells for extracting a correlation of features of training time-sequences to presence of a respiratory event in the training time-sequences.

The use of LSTM cells allows the machine learning models to model temporal aspects in the training time-sequences which enables the machine learning models to extract relevant temporal features and interactions in order to detect respiratory events. In particular, LSTM cells provide a powerful tool for extracting and using temporal information.

According to an embodiment, the method further comprises forming unique data sets to be used in training the plurality of machine learning models, wherein the forming of unique data sets comprises balanced bootstrapping of acquired training time-sequences to combine positive time-sequences including a respiratory event, re-used between different data sets, with negative time-sequences not including a respiratory event, wherein at least a plurality of the negative time-sequences are dis-joint between different data sets.

By using a balanced bootstrapping of acquired training time-sequences, the training time-sequences may be divided into unique data sets such that each data set is well-balanced between positive and negative training time-sequences. The positive time-sequences may be re-used between different data sets, such that each data set comprises several positive time-sequences, whereas the negative time-sequences may be arranged in separate data sets. In this way, each data set may have a good balance between positive and negative training time-sequences, while information is not discarded in creation of the models.

Therefore, since each of a plurality of machine learning models in an ensemble of machine learning models is formed by training each model on a unique data set defined by balanced bootstrapping, the machine learning models may be formed while taking into account all training data in a balanced manner. This facilitates that the machine learning models are well-trained and that the detection of respiratory events may be performed in a robust manner.

According to a third aspect, there is provided a system for detecting a respiratory event of a subject under test, said system comprising: a bio-impedance measurement sensor for acquiring a bio-impedance measurement signal from the subject, said bio-impedance measurement signal being dependent on respiratory action of the subject; and a processing unit, which is configured to: receive the bio-impedance measurement signal; extract at least one time-sequence of the bio-impedance measurement signal; and for each of the extracted time-sequences: compare the bio-impedance measurement signal with each of a plurality of machine learning models in an ensemble of machine learning models so as to form a set of predictions of occurrence of a respiratory event, wherein each prediction in the set is based on comparing the bio-impedance measurement signal with one machine learning model, wherein each model correlates features of time-sequences of a bio-impedance measurement signal with presence of a respiratory event in the time-sequences of the bio-impedance measurement signal and wherein each model is trained on a unique data set of training time-sequences; and decide whether a respiratory event occurs in the extracted time-sequence based on the set of predictions.

Effects and features of this third aspect are largely analogous to those described above in connection with the first and second aspects. Embodiments mentioned in relation to the first and second aspects are largely compatible with the third aspect.

The system may thus comprise relatively simple equipment, including a bio-impedance measurement sensor, for acquiring of measurement signals from a subject in order to detect respiration events of the subject in a reliable and robust manner.

The system may further comprise a processing unit for processing of the acquired bio-impedance measurement signal so that the system may decide whether respiratory event(s) occur in the acquired bio-impedance measurement signal.

The bio-impedance measurement sensor may be configured to be arranged in relation to the subject for facilitating acquisition of the bio-impedance measurement signal. In this regard, the bio-impedance measurement sensor may be arranged in a unit, which may be attachable to a body part of the subject for arranging the bio-impedance measurement sensor in contact with skin of the subject. For instance, the bio-impedance measurement sensor may be arranged in a patch for attachment to skin of the subject or in a belt for being strapped around a body part, such as the thorax, of the subject.

According to an embodiment, the system further comprises a housing, wherein the bio-impedance measurement sensor and the processing unit are arranged in the housing.

This implies that the system may be embedded in a single physical unit, which provides a small form factor of the system. Also, all parts of the system in a single housing may be set up in relation to each other such that no set-up of the system may be necessary by a user before taking the system into use.

According to another embodiment, the system further comprises a housing, wherein the bio-impedance measurement sensor is arranged in the housing, wherein the system further comprises a communication unit arranged in the housing, wherein the communication unit is configured to transmit the bio-impedance measurement signal to the processing unit.

The system may thus comprise a plurality of physical units. The processing unit may be arranged in one of these units, which may be attached to or worn by the subject. The processing unit may be arranged in a central unit, which may be arranged to be mounted in close relation to a measurement setting, such as mounted to a bed frame, or which may simply be arranged to be positioned nearby, such as on a bed stand.

The communication of the bio-impedance measurement signal to the processing unit may be performed through wired or wireless communication.

It should also be realized that the communication unit may be configured to communicate the bio-impedance measurement signal, e.g. via a telecommunication or computer network, to a processing unit, which may be arranged in a remote location. Thus, the processing unit may even be arranged "in the cloud".

According to another embodiment, the system may further comprise a storage unit for storing bio-impedance measurements. Thus, the system may be configured to acquire bio-impedance measurement signals from the subject and may store the bio-impedance measurements in the storage unit. Then, the bio-impedance measurements may be transferred at a later time to a processing unit for processing of the bio-impedance measurements.

The storage unit may be arranged in a common housing with the bio-impedance measurement sensor. Thus, the bio-impedance measurements may be stored in a housing in which the bio-impedance measurement sensor is arranged. The housing need not necessarily comprise any communication unit for communicating bio-impedance measurements, which may imply that the housing may be very compact and which may also imply that costs of a unit that is to be worn by the subject may be kept down.

When bio-impedance measurements have been acquired for some time period, e.g. during a night's sleep of the subject, the bio-impedance measurements in the storage unit may be transferred to a processing unit, e.g. by physically connecting the storage unit to an external processing unit.

It should thus also be realized that processing of bio-impedance measurements need not necessarily be performed in real time. Rather, the bio-impedance measurements may be stored and post-processing of bio-impedance measurement signals acquired over a period of time may be performed.

BRIEF DESCRIPTION OF THE DRAWINGS

The above, as well as additional objects, features and advantages of the present inventive concept, will be better understood through the following illustrative and non-limiting detailed description, with reference to the appended drawings. In the drawings like reference numerals will be used for like elements unless stated otherwise.

DETAILED DESCRIPTION

Figure 1:
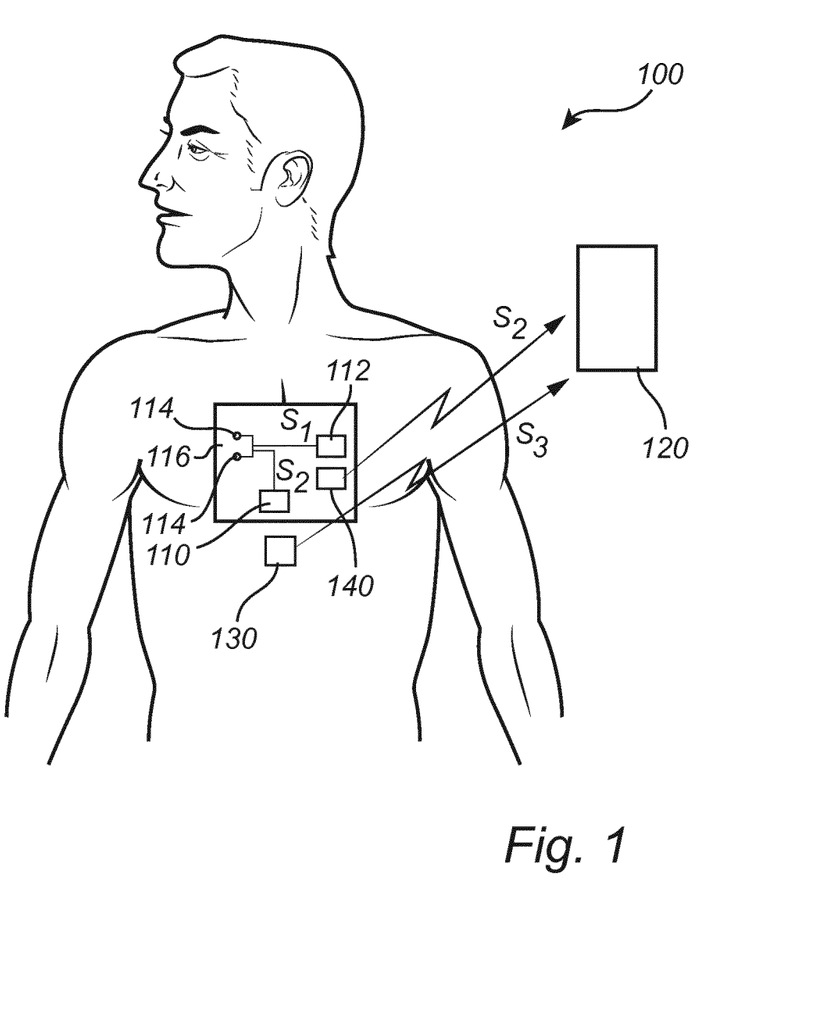
FIG. 1 is a schematic illustration of a system for respiratory monitoring according to an embodiment.

FIG. 1 illustrates a system 100 for respiratory monitoring of a subject. The system 100 may be configured to generate a current signal S1 that is to be applied to a subject and may comprise a bio-impedance measurement sensor 110 to acquire a bio-impedance measurement signal S2 providing information of the bio-impedance of the subject, which may be further processed for analyzing respiration of the subject. The bio-impedance measurement signal S2 may be provided to a processing unit 120 which may process the bio-impedance measurement signal S2 to analyze the signal.

As shown in FIG. 1, the system 100 may comprise a current signal injection module 112. The current signal injection module 112 may be configured to generate and output the current signal S1, which is to be applied to the subject. The current signal injection module 112 may comprise a current source for generating a current signal S1. The current signal injection module 112 may be configured to output an AC current signal.

The system 100 may further comprise a bio-impedance measurement sensor 110. The bio-impedance measurement sensor 110 may be configured to receive voltage input signals representing a voltage generated by the current signal S1 applied to the subject. The bio-impedance measurement sensor 110 may be configured to extract a bio-impedance measurement signal S2 from the received voltage input signals.

The bio-impedance measurement sensor 110 may comprise two or more electrodes 114, which may be arranged to be in contact with skin of the subject. The electrodes 114 may be connected to the current signal injection module 112 to receive the current signal S1 and provide the current signal through tissue of the subject. The electrodes 114 may also be connected to the bio-impedance measurement sensor 110 for providing voltage input signals that may be used for acquiring the bio-impedance measurement signal S2.

The electrodes 114 may be arranged in a bipolar arrangement, wherein the same electrodes 114 are used for providing the current signal S1 to the subject and for acquiring the voltage input signals. However, the electrodes 114 may alternatively be arranged in a tetrapolar arrangement, wherein two electrodes are used for providing the current signal S1 to the subject and two other electrodes are used for acquiring the voltage input signals.

More than two (or four) electrodes 114 may be provided, which may allow selection of which electrodes 114 to be used in a measurement, so that electrodes 114 providing highest quality bio-impedance measurement signal S2 may be selected. The selection of which electrodes 114 to be used may be performed in set-up of the system 100 or may be dynamically changed during signal acquisition e.g. when conditions for acquiring the bio-impedance signal change.

The bio-impedance measurement sensor 110 with electrodes 114 may be configured to be attached on a thorax region of the subject. The bio-impedance measurement sensor 110 may be arranged on a carrier 116 configured for being arranged on a thorax region of the subject, wherein the electrodes 114 may be mounted to be exposed on the carrier 116, such that the electrodes 114 may be arranged in contact with the skin of the subject.

The carrier 116 may for instance comprise an adhesive patch, a textile/garment being worn by the subject, or a belt, which may be configured to be attached around the torso of the subject.

When a bio-impedance measurement is performed based on electrodes 114 arranged on the thorax of a subject, chest expansion may cause a change in a current path between the electrodes 114, such that the bio-impedance is changed in relation to a respiratory effort. Also, air has a different impedance than tissue. As an amount of air present in the lungs varies during a respiratory cycle, the bio-impedance is also changed in relation to respiratory airflow. Thus, the bio-impedance measurement sensor 110 may be configured for acquisition of a bio-impedance signal S2 which holds information of respiratory activity of the subject.

The processing unit 120 may be configured to receive the bio-impedance measurement signal S2 from the bio-impedance measurement sensor 110. The processing unit 120 may be configured to process the bio-impedance measurement signal S2 for detecting occurrences of respiratory events.

The processing unit 120 may be implemented in hardware, or as any combination of software and hardware. The processing unit 120 may, for instance, be implemented as software being executed on a general-purpose computer. The system 100 may thus comprise one or more physical processors, such as a central processing unit (CPU), which may execute the instructions of one or more computer programs in order to implement functionality of the processing unit 120. Thus, the system 120 may comprise a single processing unit, which may provide a plurality of functionalities e.g. as separate threads within the processing unit 120.

The processing unit 120 may alternatively be implemented as firmware arranged e.g. in an embedded system, or as a specifically designed processing unit, such as an Application-Specific Integrated Circuit (ASIC) or a Field-Programmable Gate Array (FPGA).

The system 100 may further comprise at least one additional measurement sensor 130. The additional measurement sensor 130 may be configured to measure e.g. a body temperature of the subject, a heart rate or pulse of the subject, a respiratory rate of the subject or a blood pressure of the subject. The additional measurement sensor 130 may for instance be a temperature sensor, which may be attached to skin of the subject, an electrocardiogram (ECG) sensor comprising electrodes for detecting an ECG, a photoplethysmograph (PPG) sensor comprising light source(s) and light sensor(s) for detecting a PPG, or an accelerometer, which may be configured to detect a movement of a body part (such as the chest), which may represent cardiac or pulmonary activity.

An additional measurement signal S3 may be acquired by the additional measurement sensor 130. The additional measurement signal S3 may be used by the processing unit 120, in combination with the bio-impedance measurement signal S2 for detecting occurrence(s) of respiratory events.

The system 100 may comprise one or more housings, in which the bio-impedance measurement sensor 110, the processing unit 120 and the at least one additional measurement sensor 130 may be arranged. The housings may be connected by wires for allowing communication between the sensors 110, 130 and the processing unit 120. Alternatively, one or more of the sensors 110, 130 and the processing unit 120 may be set up for wireless communication. The system 100 may thus be delivered to be ready to use, e.g. in a single package with all parts of the system 100 already set up to communicate with each other.

The processing unit 120 may be arranged in a housing on the carrier 116. The at least one additional measurement sensor 130 may also be arranged on the same carrier 116.

However, in an alternative embodiment, the processing unit 120 may be arranged in a central housing, which may be separate from the carrier 116. The central housing may be configured to be mounted or arranged in a measurement setting, e.g. at a bed stand. The central housing may comprise a display, such that measurements and analysis results acquired by the system 100 may be displayed to a user.

The system 100 may further comprise a communication unit 140 arranged in the carrier 116 or in a central housing. The communication unit 140 may be configured for communication via a telecommunication or computer network. This implies that the signals S2, S3 acquired by the system 100 may be communicated to a processing unit 120, which may be arranged in a remote location. Thus, the processing unit 120 may even be arranged "in the cloud".

The system 100 may further comprise a storage unit in which bio-impedance measurements and additional measurements may be stored. The acquired bio-impedance measurements and additional measurements may thus be acquired for a period of time and the measurement results acquired during the period of time may be stored in the system 100, e.g. in a storage unit which may be arranged in the housing on the carrier 116.

The bio-impedance measurement results and the additional measurement results may be transferred from the storage unit to a processing unit for post-processing of the measurement results any time after the measurement results have been acquired. This implies that the system 100 does not necessarily comprise a communication unit, since the measurement results may be transferred from the storage unit by physically connecting the storage unit to the processing unit or an intermediate unit, which may transfer the measurement results to the processing unit.

The bio-impedance measurements and the additional measurements may also be separately acquired and even stored in separate storage units. The bio-impedance measurements and the additional measurements may then be synchronized in time during post-processing of the measurement results.

The system 100 comprises relatively simple and inexpensive equipment, which may allow use of the system 100 in a home environment of a subject. This implies that the system 100 may be used for acquiring data over large time periods, such as acquiring data over multiple nights when analyzing sleep disorders, since the system 100 may be used in the home of the patient and a patient does not need to spend time at a laboratory, with limited availability. Thus, large amounts of data may be gathered for a subject, which may facilitate making better analysis of a subject's condition.

The processing unit 120 may be configured to extract at least one time-sequence of the bio-impedance measurement signal S2. A bio-impedance measurement signal S2 may be divided into a sequence of time-sequences, wherein sequential time-sequences may possibly be overlapping. The time-sequence may be analyzed in order to determine whether a respiratory event occurs within the time-sequence. By analyzing a plurality of time-sequences, it may then be possible to determine frequency of respiratory events and analyze a subject's condition based on the frequency.

A duration of a time-sequence may be selected to be within a range of e.g. 10-180 seconds. According to an embodiment, the duration may be selected to be within a range of 20-60 seconds. According to yet another embodiment, the duration may be selected to be 30 seconds. A duration of a time-sequence may be set sufficiently long to cover the duration of the respiratory event, but not too long so that a relative effect of the respiratory event may be hidden within the time-sequence.

The processing unit 120 may further be configured to extract at least one time-sequence of the one or more additional measurement signals S3.

An extracted time-sequence of the bio-impedance measurement signal S2 and/or an extracted time-sequence of the one or more additional measurement signals S3 may be compared to a plurality of machine learning models in an ensemble of machine learning models so as to form a set of predictions of occurrence of a respiratory event in the extracted time-sequence. The processing unit 120 may thus access an ensemble of machine learning models, which may e.g. be stored in a memory associated with the processing unit 120, so as to compare the extracted time-sequence with the stored plurality of machine learning models.

The plurality of machine learning models may be configured to correlate features of time-sequences of a bio-impedance measurement signal S2 and/or features of time-sequences of one or more additional measurement signals S3 with presence of a respiratory event. Each model may be trained on a unique data set of training time-sequences, such that each model provides a separately trained manner of identifying respiratory events.

The processing of the extracted time-sequence further comprises deciding whether a respiratory event occurs in the extracted time-sequence based on the set of predictions. Thanks to the use of a plurality of machine learning models, the detecting of respiratory events is robust, while using relatively simple measurements on the subject.

Figure 2:
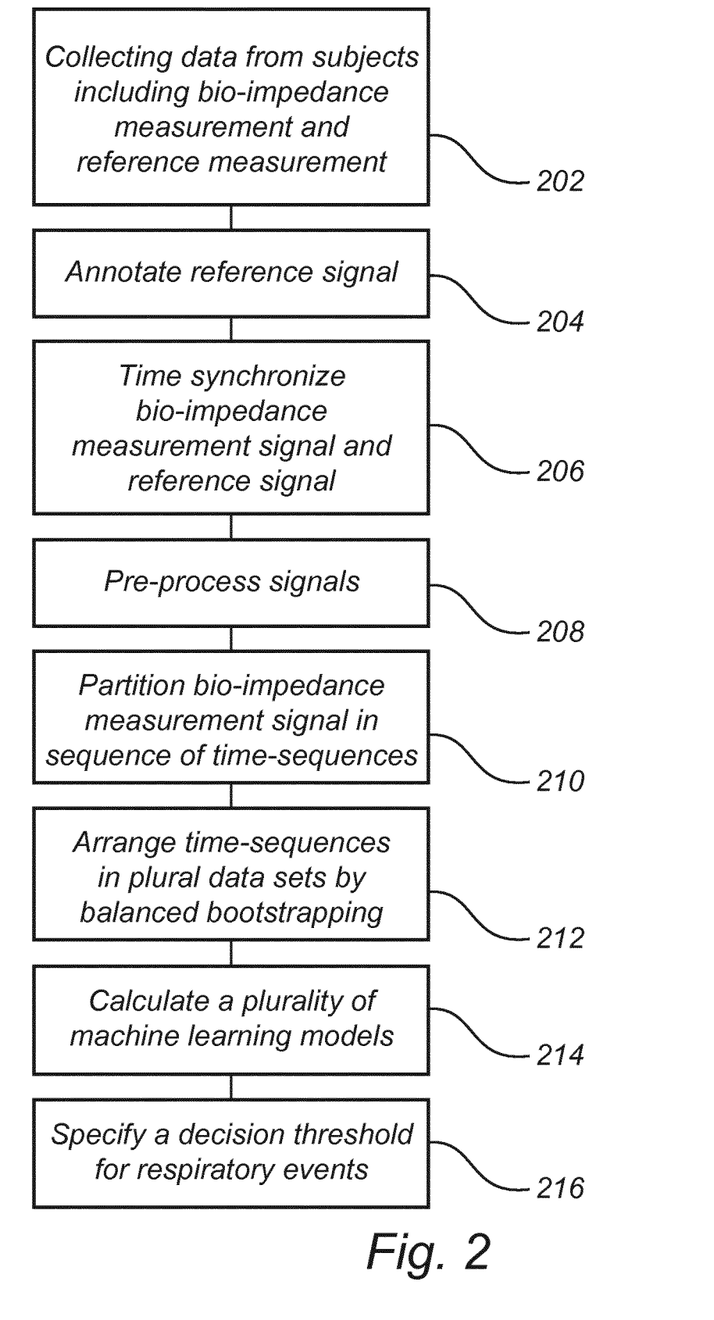
FIG. 2 is a schematic flow chart of a training phase method for generating a plurality of machine learning models for detecting a respiratory event.

Referring now to FIG. 2, a training phase method for generating a plurality of machine learning models will be described.

The training phase method may comprise collecting 202 data from subjects. The collecting of data may comprise acquisition of a bio-impedance measurement signal S2 and, possibly, one or more additional measurement signals S3. Simultaneously with the acquisition of the bio-impedance measurement signal S2 and the one or more additional measurement signals S3, a reference signal which may provide a reliable indication of respiratory events is acquired. For instance, PSG signals may be acquired, which may require complex and expensive hardware, but may provide a reliable detection of respiratory events.

The reference signal may be analyzed for annotating 204 the reference signal to indicate respiratory events. The analysis of reference signal may be performed using a reliable technology for automated analysis of the reference signal. Alternatively, the analysis of reference signal may be performed by manual annotation, e.g. by manual annotation of PSG data using official guidelines, such as American Academy of Sleep Medicine (AASM) guidelines.

The annotation of reference signal may provide indication of time points when respiratory events occurs. Each respiratory event may further be classified based on a type of respiratory event, such as apnea and hypopnea, such as obstructive sleep apnea (OSA), central apnea (CA), obstructive hypopnea, and central hypopnea, and combinations thereof.

The acquired signals, i.e. the bio-impedance measurement signal S2, the one or more additional measurement signals S3, and the reference signal, may be time synchronized 206 to ensure that the annotation of the reference signal may be correctly applied to the information in the bio-impedance measurement signal S2 and the one or more additional measurement signals S3. The time synchronization may be performed before or after the annotation of the reference signal.

One or more of the acquired signals, i.e. the bio-impedance measurement signal S2, the one or more additional measurement signals S3, and the reference signal, may further be preprocessed 208. The preprocessing of signals may be used for noise removal and extracting relevant respiratory information in a signal which may include information associated with other sources, such as cardiac activity.

The bio-impedance measurement signal S2 and the one or more additional measurement signals S3 may then be partitioned 210 in a sequence of time-sequences (or epochs). The epochs may be overlapping.

Each epoch may be labeled based on the annotation of the reference signal, such that, for each epoch there is an indication whether a respiratory event occurs, e.g. a "0" indicating that no respiratory event is occurring and a "1" indicating that a respiratory event is occurring. The labelling may be performed generally for any respiratory event occurring or may be performed for each type of respiratory event, such that a plurality of labels (0/1) may be set for a plurality of types of respiratory events.

The epochs are to be used as training time-sequences for training machine learning models. However, there is an imbalance in that a collected data set will comprise a much larger number of negative epochs (no respiratory event occurring) than positive epochs (respiratory event occurring).

The epochs are arranged 212 in a plurality of training data sets to handle the imbalance through balanced bootstrapping. The positive epochs are re-used between different data sets, whereas at least a plurality of negative epochs are dis-joint between different data sets. In this manner, all epochs may be used, while, for each data set, there is a good balance between positive and negative epochs.

The plurality of training data sets is then used to calculate 214 a plurality of machine learning models. Each model may be trained using one of the data sets.

According to one embodiment, Long-Short Term Memory (LSTM) cells may be used for modelling the detection of respiratory events. This provides a powerful tool for extracting and using temporal information. However, other modelling schemes may be used, such as Gated Recurrent Unit (GRU), or another scheme based on a Recurrent Neural Network (RNN).

Each model may be trained to generate a prediction of occurrence of a respiratory event. The plurality of machine learning models may further be used for averaging predictions of individual models into an aggregate model that may output a single score (e.g. a mean of probabilities).

Finally, the training phase method may include specifying 216 a decision threshold based on a set of predictions for enabling a decision whether a respiratory event occurs based on whether an aggregate score of the machine learning models is above or below the decision threshold.

Figure 3:
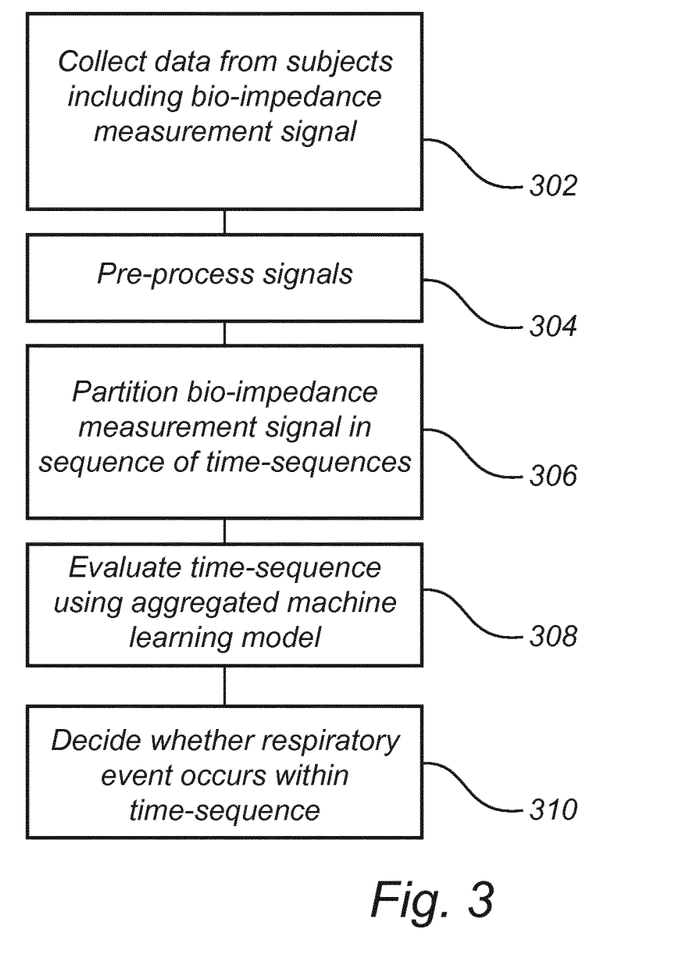
FIG. 3 is a schematic flow chart of a deployment phase method for detecting respiratory events.

Referring now to FIG. 3, a deployment phase method for using the plurality of machine learning models in detecting of respiratory events will be described.

In the deployment phase, the detection of respiratory events is made based on only the bio-impedance measurement signal S2, possibly in combination with the one or more additional measurement signals S3. The reference signal is no longer needed, as the system 100 has now been trained for detecting respiratory events based on the bio-impedance measurement signal S2, possibly in combination with the one or more additional measurement signals S3.

Thus, the method comprises collecting 302 data from a subject under test by acquisition of the bio-impedance measurement signal S2, possibly in combination with the one or more additional measurement signals S3.

The method may further comprise preprocessing 304 the bio-impedance measurement signal S2 and the one or more additional measurement signals S3. Similar to the training phase method, the preprocessing of signals may be used for noise removal and extracting relevant respiratory information in a signal.

The bio-impedance measurement signal S2 and the one or more additional measurement signals S3 may then be partitioned 306 in a sequence of time-sequences (or epochs). The epochs may be overlapping.

Each epoch may then be analyzed in order to determine whether a respiratory event is occurring within the epoch. The analysis may comprise evaluating 308 the epoch using an aggregated machine learning model, as generated according to the above description. Thus, the epoch may be compared to each model in a plurality of machine learning models for determining a set of predictions of occurrence of a respiratory event within the epoch. The set of predictions may be aggregated into a single, combined score for a probability of a respiratory event occurring.

Then, a decision may be taken 310 whether a respiratory event occurs within the epoch. The decision may be based on determining whether the aggregated score obtained by the machine learning model exceeds a set threshold or not.

Now, for illustrative purposes, a specific example of training and using machine learning models will be described.

A system 100 which is trained is configured to record three types of signals: bio-impedance (BioZ), ElectroCardioGraphy (ECG) and acceleration. The bio-impedance is measured at 1024 Hz, the ECG is measured at 512 Hz and the acceleration, consisting of 3 separate components, is measured at 32 Hz.

In the training phase, these signals are combined with the signals from the PSG device recorded at 200 Hz. However, a significant frequency shift is visible after a while as sampling frequencies of the signals are not exact. Furthermore, when the system 100 and the PSG device are attached to the patient, they may not be activated at the same time. Hence, accurate time-alignment of both devices may be needed.

To align the signals of the system 100 and the PSG device in time, the ECG signal is used as it is available in both devices. However, it should be realized that the time alignment may be based on other information.

In the training phase, data from subjects suffering from respiratory events, such as suspected sleep apnea patients, is collected using the PSG device and the system 100 simultaneously. The machine learning algorithms are then trained using both types of data.

In the deployment phase, these machine learning models are used to predict the occurrence of sleep apnea in data of new, unseen subjects, wherein the data is recorded using only the system 100.

The preprocessing of bio-impedance measurement signals S2 may convert raw bio-impedance input signals into epochs comprising relevant information. A complex-valued bio-impedance measurement signal may thus be transformed into a respiratory signal.

The preprocessing may include that the raw bio-impedance measurement signal is subsampled to a sampling frequency of 5 Hz after which a magnitude of the complex-valued bio-impedance signal is extracted. However, features may be extracted in another manner from the bio-impedance signal. For instance, just the real part of the complex-valued bio-impedance signal may be extracted.

To extract respiratory information, the bio-impedance measurement signal, in this case the bio-impedance magnitude (or real value of the bio-impedance), may in preprocessing of the signal be passed through a filter, such as a low-pass Butterworth filter. The Butterworth filter may ensure that information in the bio-impedance measurement signal S2 relating to respiration of the subject is extracted in a robust manner from other information in the bio-impedance measurement signal S2, such as cardiac activity information.

The Butterworth filter may be a fourth order Butterworth filter with cutoff frequency of 0.7 Hz, but it should be realized that other settings may be used.

The preprocessing may further include removing of motion artefacts from the filtered signal by applying a moving average filter to the filtered signal and subtracting the signal obtained from applying the moving average filter from the original filtered signal. The moving average filter may for instance have a width of 4 seconds.

After the preprocessing of the signal, an estimation of the respiratory-related bio-impedance changes in the original signal remains.

A full-length respiratory signal may be converted into 30 second epochs with a stride of 1 second in between each other, i.e. there is a major overlap between two sequential epochs (only 1 s of the signal is differing).

The values of each epoch may be standardized separately in a range of [−1; 1]. This may improve modelling capabilities of the machine learning models.

During the training phase, simultaneous measurements are gathered from the system 100 as well as from a PSG device. The data from the PSG device may be used to create an apnea-hypopnea annotation by a trained nurse. For each epoch of the extracted respiratory information in the system 100, an annotation is added based on the PSG annotations of the nurse. If at the end of the epoch the nurse annotated an apnea or hypopnea event, the epoch is labeled an apnea epoch. As mentioned above, different respiratory events may be distinguished. However, in other embodiments, no distinction is made in OSA, CA or hypopnea.

The epochs generated by the preprocessing normally comprise of a large majority (95%) of apnea-negative epochs and a small minority (5%) of apnea-positive epochs leading to an imbalanced data set. As the machine learning models in the modelling phase may be sensitive to class imbalance, data balancing is advantageous in allowing a data set to be properly modelled.

Figure 4A:
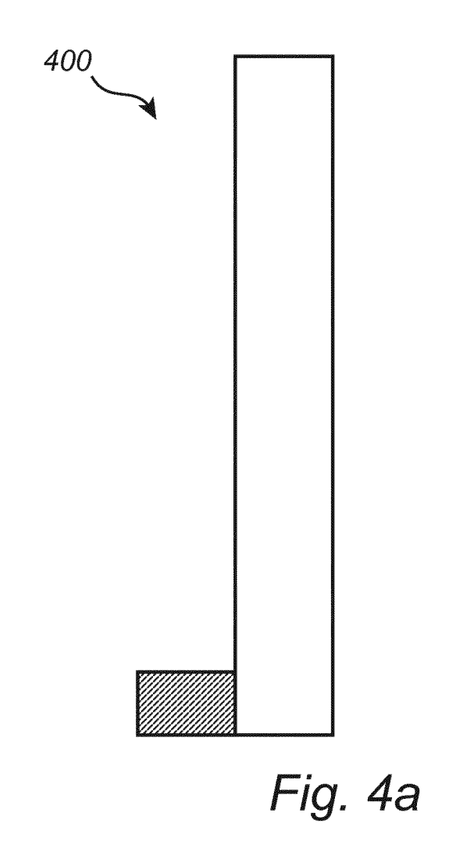
FIGS. 4a-c is a schematic view of a balanced bootstrapping method for generating balanced data sets.
Figure 4B:
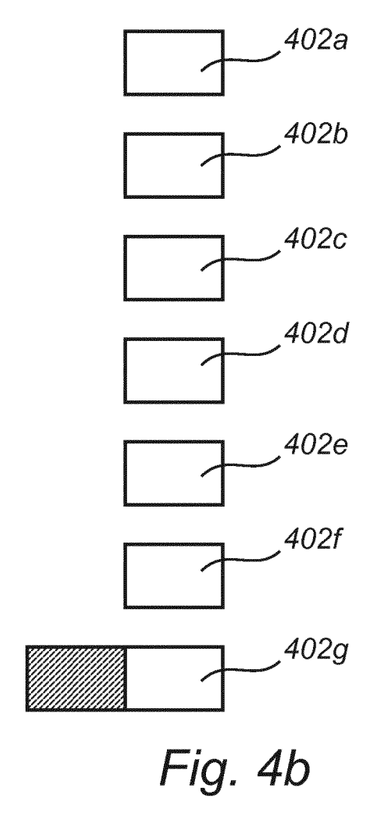
Figure 4C:
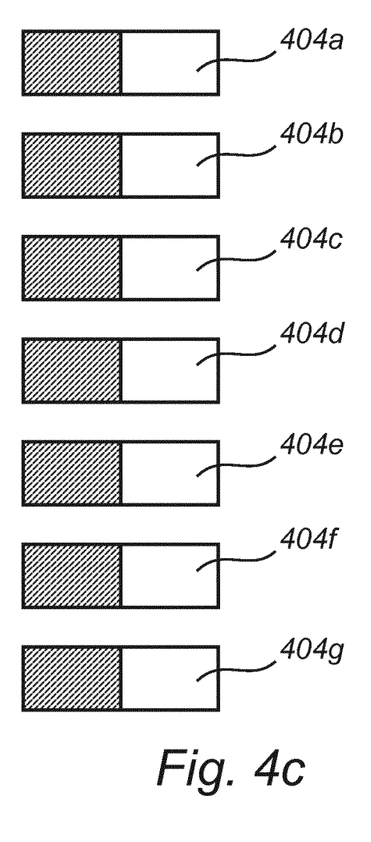

In the training phase, a balanced bootstrapping method is used. As illustrated in FIGS. 4a-c, with the balanced bootstrapping method, the large imbalanced data set 400, illustrated in FIG. 4a, is split up into several smaller balanced data sets 404a-g.

First, the majority class (indicated by white areas in FIGS. 4a-c) in the unbalanced data set 400 is split into subsets 402a-g with size equal to the minority class (indicated by hatched areas in FIGS. 4a-c), as illustrated in FIG. 4b. Then, the epochs of the minority class are appended to the different sets of the majority class leading to multiple balanced data sets 404a-g, as illustrated in FIG. 4c. Each data set may have all epochs from the minority class and a disjoint set of epochs from the majority class. Each of these data sets 404a-g can now be used to build a separate model.

It should be realized that not necessarily all epochs from the minority class are used in each of the balanced data sets. An apnea-positive epoch may be re-used in several data sets 404a-g, but not necessarily re-used in every data set 404a-g. Also, not necessarily all majority epochs are used in a single data set. Rather, one or more majority epochs may be re-used in the data sets 404a-g, such that the sets of epochs from the majority class are not completely dis-joint.

Each of the data sets 404a-g generated in the balanced bootstrapping procedure is modelled individually. As the data being modelled comprises a lot of temporal information, neural networks with LSTM cells may be used as these are powerful tools for extracting and using temporal information.

Figure 5:
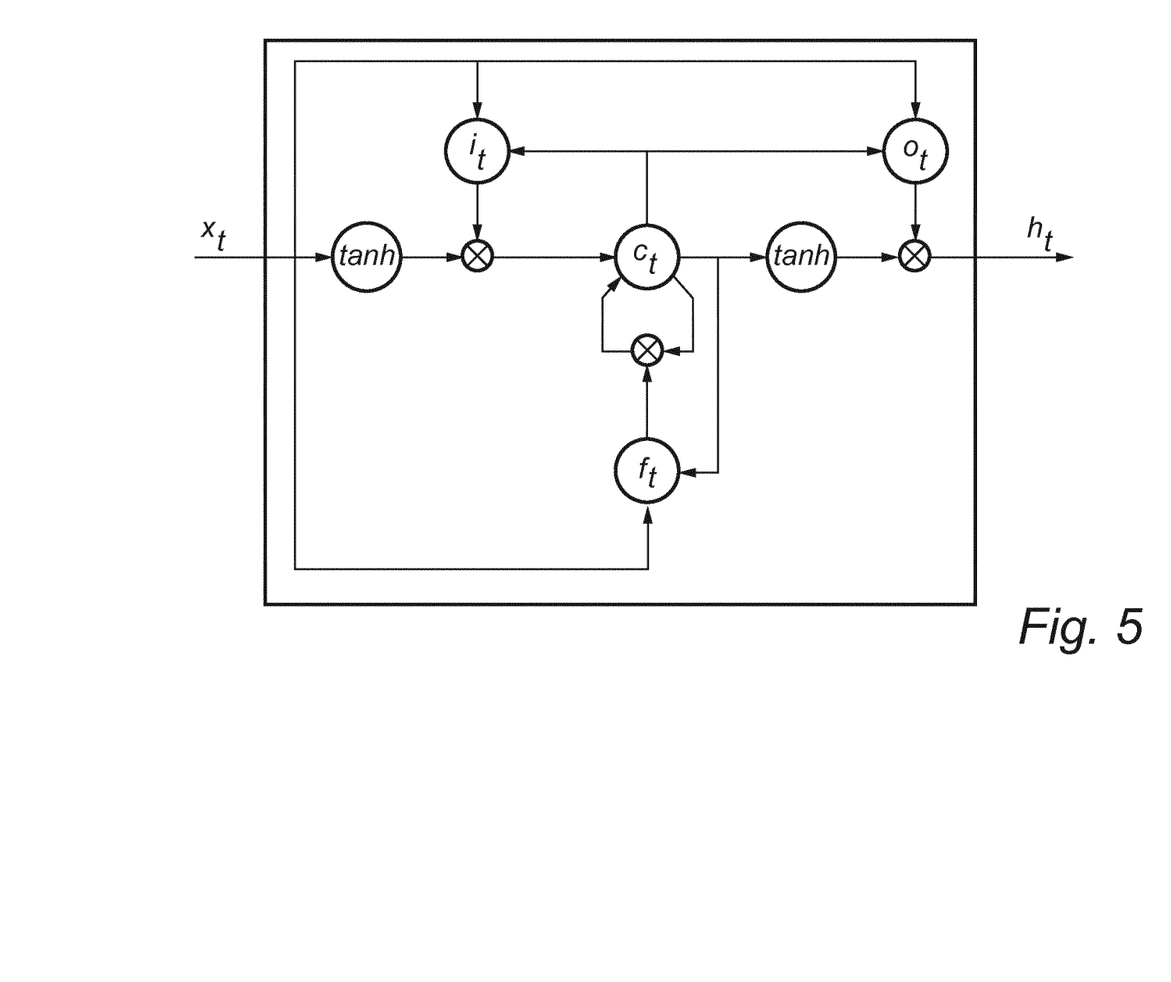
FIG. 5 is a flow chart of a Long-Short Term Memory (LSTM) cell.

A flowchart of an embodiment of the LSTM cell is shown in FIG. 5 and corresponding equations are given by:

$$i_t = \sigma(W_{xi}x_t + W_{hi}h_{t-1} + W_{ci}c_{t-1} + b_i)$$

$$f_t = \sigma(W_{xf}x_t + W_{hf}h_{t-1} + W_{cf}c_{t-1} + b_f)$$

$$c_t = f_t c_{t-1} + i_t \tanh(W_{xc}x_t + W_{hc}h_{t-1} + b_c)$$

$$o_t = \sigma(W_{xo}x_t + W_{ho}h_{t-1} + W_{co}c_t + b_o)$$

$$h_t = o_t \tanh(c_t),$$

wherein x represents the input sequence, h represents the hidden sequence, t represents a time point in the sequences, c represents the cell vector and i, f and o represent the input gate, forget gate and the output gate, respectively, the σ operator is the logistic sigmoid function, the b terms are the bias terms and the matrices W are weight matrices between two entities.

The LSTM cells may automatically extract relevant feature data through time.

In the example, the network architecture used comprises 50 base LSTM cells followed by a dropout layer with dropout probability 0.2. Adding a dropout layer allows for a more powerful generalization of the model to unseen data. After the dropout layer, 10 regular dense nodes are added followed by another dropout layer with dropout probability 0.2. Finally, a single dense neural network node is appended with sigmoid activation function for classification of epochs.

The network may be trained with minibatches of 32 epochs consisting of 16 positive and 16 negative epochs using the binary crossentropy loss function which is optimized using the adadelta optimiser. Gradient clipping is applied to a value of 100.

The balanced bootstrapping procedure has created several distinct data sets for models to be trained on. In the modelling stage, each of these models is trained individually. To test a new epoch, it may be tested with any of these models. However, due to random differences in the models and differences in the training data sets, these models will have slightly different predictions. As these predictions represent probabilities, we can take a mean of these predictions to get a mean probability of the output. The aggregated output from all models provides a more robust estimate of the true probability of apnea for that epoch.

This aggregated estimate can be further fine-tuned to specific needs of an application for detecting respiratory events.

For instance, an epoch may be determined as comprising an apnea event by determining if the probability of apnea is larger than 0.5. However, it may be beneficial to also tune this decision threshold as indicating a false negative may be worse than indicating a false positive. Hence, the decision threshold may be tuned by varying the decision threshold in the range [0; 1]. Based on such tuning, resulting sensitivity and specificity scores may be computed. A most beneficial decision threshold (largest sensitivity and specificity) may then be chosen as the final decision threshold value t.

To get a measure of severity of apnea/hypopnea of a patient, the Apnea Hypopnea Index (AHI) is computed as the number of respiratory events divided by the total sleep time following the official AASM guidelines. As each epoch ends 1 second after the other, the method may provide a prediction of the probability of sleep apnea for each second of the signal. If the probability is larger than t, a particular second in the signal is flagged as a respiratory event. These generated annotations are then used to compute the AHI. Using this AHI score, patients may be classified with normal breathing, mild sleep apnea, moderate sleep apnea or severe sleep apnea.

In the above the inventive concept has mainly been described with reference to a limited number of examples. However, as is readily appreciated by a person skilled in the art, other examples than the ones disclosed above are equally possible within the scope of the inventive concept, as defined by the appended claims.

The invention claimed is:

1. A method for detecting a respiratory event of a subject, said method comprising:
 receiving a bio-impedance measurement signal from the subject, said bio-impedance measurement signal being dependent on respiratory action of the subject;
 extracting at least one time-sequence of the bio-impedance measurement signal; and
 for each of the extracted time-sequences:
  by means of a processing unit, comparing the bio-impedance measurement signal with each of a plurality of machine learning models in an ensemble of machine learning models so as to form a set of predictions of occurrence of a respiratory event, wherein each prediction in the set is based on comparing the bio-impedance measurement signal with one machine learning model, wherein each model correlates features of time-sequences of a bio-impedance measurement signal with presence of a respiratory event in the time-sequences of the bio-impedance measurement signal and wherein each model is trained on a unique data set of training time-sequences; and
  determining whether a respiratory event occurred in the extracted time-sequence based on the set of predictions.

2. The method according to claim 1, wherein the bio-impedance measurement signal is compared with each of a plurality of machine learning models in an ensemble of machine learning models formed by neural networks with Long-Short Term Memory, LSTM, cells analyzing the unique data sets of training time-sequences.

3. The method according to claim 1, wherein the bio-impedance measurement signal is compared with each of a plurality of machine learning models in an ensemble of machine learning models formed by training each model on a unique data set that has been formed by balanced bootstrapping of acquired training time-sequences to combine positive time-sequences including a respiratory event, re-used between different data sets, with negative time-sequences not including a respiratory event, wherein at least a plurality of the negative time-sequences are disjoint between different data sets.

4. The method according to claim 1, wherein the data set of training time-sequences have been acquired from the subject for whom respiratory events are detected.

5. The method according to claim 1, further comprising receiving an additional measurement signal;
 extracting at least one time-sequence of the additional measurement signal, wherein the at least one time-sequence of the additional measurement signal corresponds to a simultaneous time period with the at least one time-sequence of the bio-impedance measurement signal; and
 for each of the extracted time-sequences:
  comparing the bio-impedance measurement signal and the additional measurement signal with each of a plurality of machine learning models in an ensemble of machine learning models so as to form predictions being included in the set of predictions of occurrence of a respiratory event.

6. The method according to claim 1, further comprising pre-processing the received bio-impedance measurement signal.

7. The method according to claim 1, wherein the extracting of at least one time-sequence of the bio-impedance measurement signal comprises extracting a plurality of sequential time-sequences of the bio-impedance measurement signal.

8. The method according to claim 7, further comprising determining a measure of respiratory condition of the subject based on comparing a number of time-sequences, for which a decision that a respiratory event occurred has been taken, to a relevant duration period of the bio-impedance measurement signal.

9. The method according to claim 1, wherein the comparing of the bio-impedance measurement signal with each of a plurality of machine learning models determines a plurality of sets of predictions for occurrences of different respiratory events, and wherein said determining whether a respiratory event occurred is performed for each set of predictions, wherein the method further comprising outputting a prediction of occurrence of a respiratory even.

10. A method for forming a model for detecting a respiratory event of a subject, said method comprising:
 receiving bio-impedance measurement signals from one or more subjects, said bio-impedance measurement signal being dependent on respiratory action of the subject;
 extracting a plurality of training time-sequences of the bio-impedance measurement signals;
 receiving information of occurrences of respiratory events, which information is synchronized with the plurality of training time-sequences so as to classify the training time-sequences as positive time-sequences representing a respiratory event or negative time-sequences not representing a respiratory event;
 determining a plurality of machine learning models to form an ensemble of machine learning models, wherein each model correlates features of time-sequences of a bio-impedance measurement signal with presence of a respiratory event in the time-sequences of the bio-impedance measurement signal and wherein each model is trained on a unique data set of the plurality of training time-sequences.

11. The method according to claim 10, wherein the determining of the plurality of machine learning models comprises using neural networks with Long-Short Term Memory, LSTM, cells for extracting a correlation of features of training time-sequences to presence of a respiratory event in the training time-sequences.

12. The method according to claim 10, further comprising forming unique data sets to be used in training the plurality of machine learning models, wherein the forming of unique data sets comprises balanced bootstrapping of acquired training time-sequences to combine positive time-sequences including a respiratory event, re-used between different data sets, with negative time-sequences not including a respiratory event, wherein at least a plurality of the negative time-sequences are disjoint between different data sets.

13. A system for detecting a respiratory event of a subject under test, said system comprising:
   a bio-impedance measurement sensor for acquiring a bio-impedance measurement signal from the subject, said bio-impedance measurement signal being dependent on respiratory action of the subject; and
   a processing unit which is configured to:
   receive the bio-impedance measurement signal;
   extract at least one time-sequence of the bio-impedance measurement signal; and
   for each of the extracted time-sequences:
      compare the bio-impedance measurement signal with each of a plurality of machine learning models in an ensemble of machine learning models so as to form a set of predictions of occurrence of a respiratory event, wherein each prediction in the set is based on comparing the bio-impedance measurement signal with one machine learning model, wherein each model correlates features of time-sequences of a bio-impedance measurement signal with presence of a respiratory event in the time-sequences of the bio-impedance measurement signal and wherein each model is trained on a unique data set of training time-sequences; and
      determine whether a respiratory event occurred in the extracted time-sequence based on the set of predictions.

14. The system according to claim 13, further comprising a housing, wherein the bio-impedance measurement sensor and the processing unit are arranged in the housing.

15. The system according to claim 13, further comprising a housing, wherein the bio-impedance measurement sensor is arranged in the housing, wherein the system further comprises a communication unit arranged in the housing, wherein the communication unit is configured to transmit the bio-impedance measurement signal to the processing unit.

* * * * *